United States Patent
Bak et al.

Patent Number: 5,455,319
Date of Patent: Oct. 3, 1995

[54] PROCESS FOR POLYMERIZING VINYL CHLORIDE POLYMERS WITH IODINATED CHAIN TRANSFER AGENTS

[75] Inventors: Philip I. Bak, Amherst; Gregory P. Bidinger, Akron; Ross J. Cozens, Strongsville; Paul R. Klich, Lyndhurst; Lance A. Mayer, Strongsville, all of Ohio

[73] Assignee: The Geon Company, Independence, Ohio

[21] Appl. No.: 269,464

[22] Filed: Jun. 30, 1994

Related U.S. Application Data

[63] Continuation-in-part of Ser. No. 34,981, Mar. 22, 1993, abandoned.

[51] Int. Cl.$^6$ ................ C08F 2/20; C08F 2/38
[52] U.S. Cl. ................ 526/206; 526/344.2
[58] Field of Search ................ 526/206

[56] References Cited

U.S. PATENT DOCUMENTS

| | | | |
|---|---|---|---|
| 2,647,107 | 7/1953 | Barnes | 526/206 |
| 4,696,983 | 9/1987 | Cohen | 526/62 |

FOREIGN PATENT DOCUMENTS 1073594   6/1967   United Kingdom.

*Primary Examiner*—Christopher Henderson
*Attorney, Agent, or Firm*—Miles B. Dearth

[57] ABSTRACT

The present invention to a method of synthesizing poly(vinyl halide) by means of a free radical polymerization which mimics a "living" radical polymerization in the presence of an iodine containing chain transfer agent containing at least one iodine atom bonded to a primary carbon atom and having the formula:

R—CH$_2$ I                          (I)

R—CHX I                             (II),

R—CH(X)—CH$_2$ I                    (III),

R—CH(X)—CHX I                       (IV), or

R—CH(X)—CH$_2$ —CHX I               (V), wherein X is fluorine, chlorine, bromine, or iodine, R is hydrogen, $C_1$, $C_2$, $C_3$, $C_4$, $C_5$ alkyl, any of which are linear or branched, cyanoalkyl, cyclohexyl, methyl cyclohexyl, phenyl, benzyl, and halogenated or oxygenated derivatives thereof.

In accordance with the invention there is further provided a method of synthesizing 1-halo-1-iodoethane by reacting hydrogen iodide with vinyl chloride or vinyl fluoride in the presence of an iodine generating catalyst under certain specified conditions. The resulting product of the reaction is a high yield, high purity 1-chloro-1-iodoethane or 1-fluoro-1-iodoethane. The poly(vinyl halide) resin is obtainable under conventional temperatures of polymerization and the chain transfer agents included herein perform consistently over repeated runs, hence useful for commercial manufacturing. The resin obtained has reduced molecular weight and polydispersity, good thermal stability, and enhanced mechanical properties, compared to poly(vinyl halide) conventionally formed by free radical methods at higher temperatures and/or with the use of conventional chain transfer agents for vinyl halide polymer.

1 Claim, 2 Drawing Sheets

VCM Polymerization Using Iodoform
Mw, Mn and Polydispersity vs. Time

VCM Polymerization Using 1-Chloro-1-iodoethane

Mw, Mn and Polydispersity vs. Conversion

VCM Polymerization Using Iodoform
Mw, Mn and Polydispersity vs. Time

PROCESS FOR POLYMERIZING VINYL CHLORIDE POLYMERS WITH IODINATED CHAIN TRANSFER AGENTS

This is a continuation-in-part of Ser. No. 08/034,981 field Mar. 22, 1993, now abandoned.

BACKGROUND OF THE INVENTION

1. Field of Invention

The present invention relates to a simple, efficient and reliable method of obtaining novel poly(vinyl halide) resins having reduced molecular weight, low polydispersity, and good thermal stability by mimicking a "living" radical polymerization mechanism.

2. Description of the Art

The addition of hydrogen iodide to vinyl chloride was first described by Kharasch and Hannum in an article in 1934. The article, entitled "The Peroxide Effect in the Addition of Reagents to Unsaturated Compounds IV. The Addition of Halogen Acids to Vinyl Chloride", *J. American Chem. Soc.*, 56, (1934) p. 712 described the addition of various halogen acids such as hydrogen iodide to vinyl chloride. In particular, Kharasch et. al. discuss the addition of 0.12 moles of hydrogen iodide to 0.1 mole of vinyl chloride in a reactor. Kharasch et. al. were studying the effects of peroxides on reactions which occur via a carbonation process in contrast to the present invention for free radical processes.

An attempt was made to reproduce the work of Kharasch and Hannum using pure reagents. Using the Kharasch procedure, there was no 1-chloro-1-iodoethane synthesized. However, applicants have discovered a novel process for synthesizing 1-chloro-1-iodoethane. The 1-chloro-1-iodoethane is useful as an iodine containing chain transfer agent in the polymerization of vinyl chloride, resulting in a vinyl chloride polymer having good thermal stability along with low molecular weight and low polydispersity.

Logothetis, in an article in *Progressive Polymer Science Vol.* 14, 1989, pp 251–296 Pergammon Press p/c describes the use of iodofluorohydrocarbons in radical polymerizations of fluorine containing monomers. Lower polydispersity elastomer fluoropolymers were reported using perfluoroalkyl iodide transfer agents.

Similarly, Tatemoto et. al. in U.S. Pat. No. 4,158,678 have disclosed segmented polymers and their formation using at least one fluorine containing segment. The segmented polymers comprise an iodine atom liberated from an iodinated compound.

German Patent No. 2,045,491 to Klinkenberg and Schrage describes the polymerization of vinyl chloride in the presence of exclusively secondary alkyl iodides at temperatures below zero degrees Celsius in order to reduce the molecular weight of the polyvinyl chloride conventionally formed at that temperature range. According to Klinkenberg et. al., vinyl chloride is polymerized at low temperature in bulk using a boron oxidizing agent as the initiator. The reaction is effected in the presence of acyclic and cyclic secondary alkyl iodides of the formula R'—CHI—R", where R' and R" are alkyl, aryl or arylalkyl or where R'+R"=—(CR$_2$)$_x$— X≧3, R=H, aryl, or arylalkyl and the total number of carbon atoms is approximately 3 to 15, preferably 3 to 6.

U.S. Pat. No. 3,983,187 to Moczygemba et. al. discloses the use of iodine or organic iodines for use as molecular weight regulators in copolymerization systems. Moczygemba et. al. use the iodine weight regulators in the suspension co-polymerization of styrene-containing monomers. This patent however is silent regarding forming poly(vinyl halide) using iodine containing chain transfer agents.

British Patent No 674,060 published in 1952 discloses polymerization of vinyl chloride in the presence of iodoform (CHI$_3$).

After many repeated trials using Iodoform it was found that widely varying results were obtained. In unexplained fashion, several trials failed to achieve any conversion of monomer or any reduction in molecular weight and no methods were obtainable to gain control over the process.

SUMMARY OF THE INVENTION

Certain iodine containing chain transfer agents have been found which are superior in the preparation of poly(vinyl halide) polymers at above 0° C. and useful for commercial production. In accordance with the present invention there is provided a novel polyvinyl halide polymer and process for preparing the poly(vinyl halide) from vinyl halide monomer by free-radical polymerization comprising (a) adding to a polymerizer, a portion or all of the vinyl halide monomer to be polymerized along with optional ethylenic unsaturated comonomer (s), (b) adding a free-radical generating initiator, and (c) polymerizing said monomer and optional comonomer(s) in the presence of a chain transfer agent containing at least one iodine atom bonded to a primary carbon atom and having the formula:

wherein X is fluorine, chlorine, bromine, or iodine, R is hydrogen, $C_1$, $C_2$, $C_3$, $C_4$, or $C_5$ alkyl, any of which are linear or branched, cyanoalkyl, cyclohexyl, methyl cyclohexyl, phenyl, benzyl, and halogenated or oxygenated derivatives thereof, and (d) and converting from 20% to 99% by weight of said monomer and optional comonomer(s) to polymer.

In accordance with the present invention there is also provided a method for synthesizing 1-halo-l-iodoethane, such as 1-chloro-1-iodoethane or 1-fluoro-1-iodoethane by reacting hydrogen iodide with vinyl chloride or vinyl fluoride in the presence of an iodine generating catalyst. The resulting product is formed in high yield, and high purity 1-halo-l-iodoethane is obtained. The method of synthesis is capable of being carried out separately or in the polymerizer prior to the polymerization of vinyl chloride or vinyl fluoride as the vinyl halide in step (a) above.

The polymerization process mimics a "pseudo-living" radical method and yields poly(vinyl halide) resin having a low polydispersity, good thermal stability, enhanced mechanical properties, and low molecular weight as compared to poly(vinyl halide) conventionally formed.

DETAILED DESCRIPTION OF THE INVENTION

Figure 1:
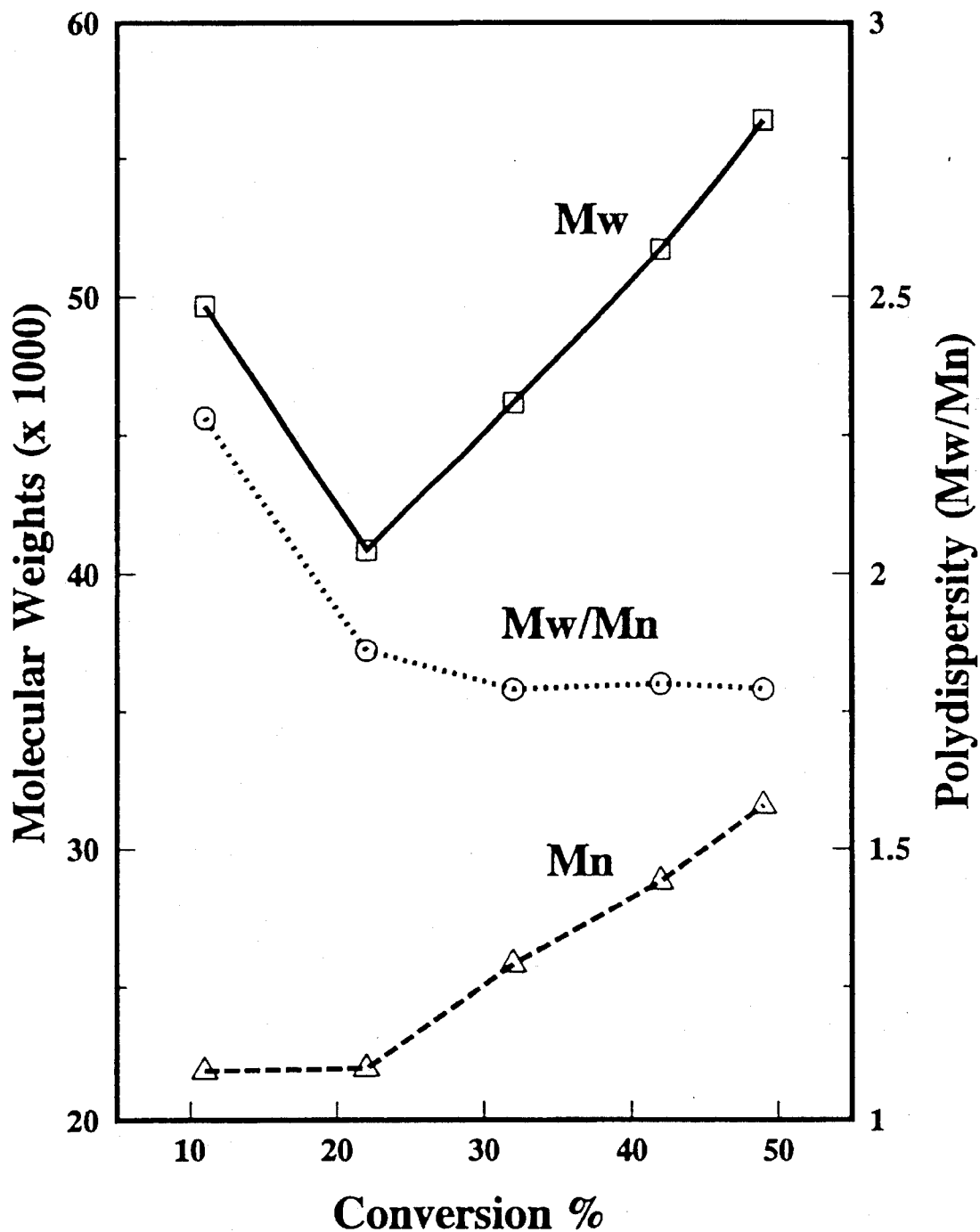
FIG. 1 is a graph showing the relationship between weight average and number average molecular weight (Mn, Mw), polydispersity and conversion during the "pseudo-living" radical polymerization of vinyl chloride using iodoform as a chain transfer agent.

Poly(vinyl halide) polymers formed by the conventional free radical process generally have a polydispersity of approximately 2.2 to approximately 3.5. The molecular weight (Mw) of conventionally formed poly(vinyl halide) ranges from about 60,000 to about 265,000. The reduction in average molecular weight by use of mercaptan transfer agent, and/or very high polymerization temperature, typically results in a decrease in thermal stability. The use of mercaptans generally increases the polydispersity of the polymer formed. There is less control of molecular weight and polydispersity using mercaptan chain transfer agent. In the free radical polymerization process, the propagating radicals have high reactivity and show a pronounced tendency to terminate by radical-radical interaction, while the vinyl halide monomer has very low reactivity. In the present invention it has been found that molecular weight increases approximately linearly with conversion and can be quite low. The desired molecular weight of the resulting polymer can be controlled because of the linear relationship to monomer conversion. Therefore, to obtain the desired molecular weight, a predetermined amount of iodine containing chain transfer agent is added to the polymerizer prior to or during the polymerization.

The subject monomers of this invention are collectively referred to as vinyl halides. Examples of vinyl halides useful for this invention are vinyl chloride, vinylidene chloride, vinyl fluoride and vinylidene fluoride, including mixtures. Other monomers copolymerizable with any vinyl halide may also be used such as a different vinyl halide, acrylates, olefins, vinyl ethers and vinyl esters, and others generally known in the art. The most preferred vinyl halides are vinyl chloride, and vinylidene chloride. The polymers of the present invention will contain greater than 50% by weight of any one or combination of the above vinyl halide monomers.

The polymerization process requires a free-radical generator, referred to as an initiator. Initiators are well known in the art, and are not the subject of this invention. The free radical initiator used is preferably capable of reacting with vinyl halide monomer to create growing polymer radical chains. Any initiator is suitable as long as it does not adversely react with the iodine containing chain transfer agent or cause liberation of the iodine from the chain transfer agent. Useful initiators for the present invention include any compounds which produce a reactive radical by the action of heat, light, or oxidation-reduction chemical reaction. Examples of the types of radical initiators include organic or inorganic peroxides or azo compounds, organic metallic compounds, and metals. The preferred radical initiators are organic peroxides. The most preferred radical initiators are peroxydicarbonates and peresters for suspension polymerization reactions. The concentration of the radical initiators should be kept to a minimum in order to suppress the bonding between radicals and to proceed with the chain extending reaction. Generally about 0.02 to 0.10 parts by weight per hundred weight parts monomer are preferred. Most preferably 0.02 to 0.05 parts of initiator per hundred parts monomer are used.

The iodine containing chain transfer agent of the present invention comprises a compound containing at least one abstractable iodine atom bonded to a primary carbon atom. In the preferred embodiment, it is believed that the iodine containing transfer agent provides a sufficiently weak bond between the iodine atom on a carbon atom ("I—C bond") so that the iodine atom can be readily abstracted by a radical producing source.

The preferred iodine containing transfer agents herein are such character so that the stability of the radical formed after transfer closely matches that of the propagating polymer radical. When this occurs, the rate of iodine transfer depends only upon the bond energy of the carbon-iodine bond, since the stabilities of the starting radical and the radical formed after the transfer are desirably similar. It has been found that iodohalohydrocarbons of the general formulae (I) to (V) below provide radicals of nearly identical stability to that of the poly(vinyl halide) propagating polymer radical.

R—CH$_2$ I (I)

R—CHX I (II),

R—CH(X)—CH$_2$ I (III),

R—CH (X)—CHX I (IV), or

R—CH (X)—CH$_2$—CHX I (V), wherein X is fluorine, chlorine, bromine, or iodine, R is a hydrogen, C$_1$, C$_2$, C$_3$, C$_4$, C$_5$ alkyl, any of which are linear or branched, cyanoalkyl, cyclohexyl, methyl cyclohexyl, phenyl, benzyl, and halogenated or oxygenated derivatives thereof. The more preferred chain transfer agents among I–V are those wherein R is hydrogen and X is chlorine.

The iodine containing transfer agent can be added to the polymerization system all at once in the beginning of the polymerization or it can be metered into the system during the polymerization. The chain transfer agent can be alternatively generated in-situ prior to the polymerization of vinyl halide monomer. The amount of chain transfer agent used can range from 0.1 to 1.0 parts by weight per 100 weight parts of monomer(s). The preferred amount used with beneficial effects ranges from 0.2 to 0.4 parts by weight per 100 weight parts of monomer.

Iodine containing transfer agents especially useful in the invention include 1-chloro-l-iodoethane, (most preferred) chloroiodomethane, 1-chloro-1,2 diiodoethane, 1,3-dichloro-1-iodopropane, 1-chloro-1-iodo-3-phenyl propane, methylcyclohexyl iodide, iodoacetonitrile, and 1,2-diiodoethane. The most preferred iodine containing transfer agent is 1, -chloro-1-iodoethane as it has been seen that this agent is superior in several aspects. It has been found that iodoform produces inconsistent results on repeated trials. Examples 20 to 51 below illustrate this limitation. There is no known method to alleviate the wide variation in results. In contrast with this, chain transfer agents which contain iodine bonded to a primary alkyl carbon and conforming to the structures of I–V above are less efficient than iodoform, however, they perform more consistently after many repetitions. This consistency is essential in providing processes which have industrial utility.

The present invention also pertains to the synthesis of 1-halo-l-iodoethane. The synthesis can occur in any of two possible ways. First, the 1-halo-1-iodoethane can be synthesized separately, purified and used as desired. Alternatively, 1-halo-1-iodoethane can be synthesized in the reaction vessel prior to the polymerization of vinyl halide monomer. This synthesis pertains to vinyl chloride or vinyl fluoride in-situ the addition of the appropriate quantity of hydrogen iodide and iodine catalyst is combined with a portion of vinyl halide monomer charged to the reaction vessel. The 1-halo-1-iodoethane generated in the reactor would then be consumed during the course of the polymerization of vinyl chloride monomer via chain transfer reactions in a process which mimics a living radical polymerization. Prior to initiation, molecular iodine liberated from the catalyst is preferably reduced by a suitable reducing agent and care must be taken to eliminate $I_2$ prior to polymerization.

The starting reagent for making 1-chloro-1-iodoethane of this invention is vinyl chloride. Correspondingly, the starting reagent for synthesizing 1-fluoro-1-iodoethane is vinyl fluoride. For the sake of brevity the synthesis will be described using vinyl chloride, but is equally adaptable with vinyl fluoride. Preferably, the vinyl chloride should be of high purity and dryness. Moreover, a slight excess of vinyl chloride monomer over hydrogen iodide is recommended to ensure complete consumption of substantially anhydrous hydrogen iodide.

The hydrogen iodide is added to vinyl chloride monomer in a reactor in the presence of an iodine catalyst. The iodine catalyst can be any iodine liberating compound and which will not in itself react with vinyl chloride or hydrogen iodide. The iodine catalyst can be an organic iodide, inorganic iodide or molecular iodine. Specific examples include KI, NaI, LiI, BrI, ClI, FI, and alkyl iodides such as $CH_3CH_2CHI_2$ and $CHI_3$. The most preferred iodine catalyst is molecular iodine. Generally, 0.1 to 2 mole % catalyst is used. Preferably, 0.1 to 1 mole % is used.

The synthesis is carried out in any reaction vessel suitable for the reaction of vinyl chloride monomer and is within the knowledge of one of ordinary skill in the art. The reaction temperature is about –75° C. to 100° C. Most preferably, the reaction temperature is about –50° C. to –45° C. The components react for approximately one to five hours in the reactor. Completion is indicated when the reactor pressure drops to the vapor pressure of the vinyl chloride. Using the instant method under specified conditions renders a yield in excess of 80 percent. The resulting 1-chloro-1-iodoethane may be purified as described below.

Iodine, which hinders vinyl halide monomer polymerization, should be removed from the 1-chloro-1-iodoethane which is formed. A suitable reducing agent such as sodium thiosulfate in aqueous solution can be mixed with the crude product followed by removal of the aqueous layer. If an organic iodide is used as the catalyst for the reaction between vinyl halide and hydrogen iodide, then the reaction product should be purified by distillation. If molecular iodine or an inorganic iodide is used as catalyst for the reaction between vinyl halide and hydrogen iodide, then the 1-chloro-1-iodoethane may be purified simply by washing with sodium thiosulfate, followed by washing with water and finally drying the product over an anhydrous drying agent, e.g., magnesium sulfate. It is suggested that the 1-chloro-1-iodoethane should be stored in the dark over copper turnings to inhibit degradation.

EXAMPLES

Example 1

Synthesis of 1-chloro-1-iodoethane

A 1-liter three-necked flask, equipped with nitrogen ("$N_2$") purge, stirrer, and cold finger condenser was assembled. The flask was immersed in a dry ice/acetone bath and the cold finger filled with the same. The flask was flushed with $N_2$. 294.3 grams vinyl chloride monomer ("VCM") (4.71 moles) were slowly added from a vessel via Teflon tubing to the flask. The VCM condensed upon contact with the cooled flask walls. 105.2 grams hydrogen iodide ("HI") (0.82 moles) were slowly bubbled through the VCM via Teflon tubing. Then, approximately 3 grams (0.01 moles) iodine crystals were added. The contents of the flask were stirred at dry ice/acetone temperature for three hours and then the bath was removed. The cold finger was maintained for an additional two hours. Excess of the reagents were permitted to evaporate as the reaction mixture warmed to room temperature. The were 131.0 grams of the product isolated as a purple liquid. The yield of 1-chloro-1-iodoethane was about 83.65%.

The purple liquid was found to lose its color in the presence of sodium thiosulfate. All of the liquid was added to a separatory funnel. An equal amount of 0.1N sodium thiosulfate was added. With continued shaking, a pale yellow organic layer (bottom layer) was obtained. The organic liquid was dried over magnesium sulfate.

Upon standing, the filtered material began to turn pink. Copper filings were added and two days later, the product was found to be a very pale yellow. A week later the color had not changed.

A 13-CNMR spectrum which exhibits signals at 22.08 and 35.07 ppm and trace impurity signals at approximately 85 and 130 ppm is consistent with the structure for 1-chloro-1-iodoethane.

Comparative Example 2

The reaction was carried out in a 1 liter glass pressure vessel, equipped with an agitator according to the method of Kharasch and Hannum discussed above. The vessel was placed under an atmosphere of nitrogen. When the vessel was cooled to around 0° C., vinyl chloride monomer (125 grams, 2 moles) was added. With the temperature held at or below 0° C., approximately 245 grams (1.9 moles) of HI vapor were transferred into the vinyl chloride using a Teflon line. The colorless mixture of liquid was then stirred and the temperature allowed to warm to room temperature over a period of approximately four hours. During that time, the reaction mixture became a pale pink in color. On subsequent evaporation of excess reagents, no measurable yield of 1-chloro-1-iodoethane was obtained.

The fact that no 1-chloro-1-iodoethane was obtained using the Kharasch et. al. method reaffirms that Applicants' iodine containing catalyst is necessary to render 1-chloro-1-iodoethane.

Polymerization of Vinyl Halide

The amount of iodine containing chain transfer agent added to the polymerization system affects the resulting molecular weight of the polymer. Generally, 0.05–0.35 parts by weight of chain transfer agent are used per one hundred parts by weight (phm) vinyl halide and optional comonomer(s) monomer. However, the exact amount will vary based upon the polymerization conditions. One of ordinary skill in the art can easily ascertain the desired amount.

The polymerization of this invention can be carried out by any conventional polymerization procedure. For example, the polymerization can be bulk, suspension, solution or emulsion. Preferably, the polymerization is carried out in suspension or bulk. However, the most preferred type of polymerization is a suspension polymerization and percent monomer conversion to polymer obtainable ranges from 20% to 99.9% by weight of monomers charged to the polymerizer.

The polymerization can be carried out at temperatures conventionally used for vinyl halide polymerization. Preferably, the temperature range will be from about 0 to about 80 degrees Celsius. The most preferred temperature range is from 40° to 60° Celsius.

The molecular weights of the poly(vinyl halide) resins formed by using the process of this invention were determined by gel permeation chromatography and calculated from retention volumes and converted to molecular weights using the universal calibration method with polystyrene standards. The analysis was performed using a 0.5% (wt./vol.) solution in tetrahydrofuran (THF) at column temperatures of 40 degrees Celsius. For low molecular weight samples, four columns were employed in a series: PL GEL 50 A, PL GEL 100 A, PL GEL 500 A, and PL GEL 1000 A. For higher molecular weight samples, three mixed-bed and one PL GEL 1000 A (Polymer Laboratories) columns were used in series. A flow rate of 1.50 ml/min. and 100 microliters sample size were used for all analyses.

A novel poly(vinyl chloride) resin having a molecular weight in the range of about 9,000 to about 30,000 and a polydispersity of less than 2.2 results using the novel process of this invention. In comparison, poly(vinyl halide) formed by the conventional free radical process at the same temperature range typically has a molecular weight in the range of about 60,000 to about 265,000. The increased control of the molecular weight of the poly(vinyl halide) resin, by the avoidance of producing the low molecular weight and high molecular weight fractions results in polymers having better thermal stability and melt flow ability. Enhanced melt flow resulting from elimination of the high molecular weight fraction enables the resins to be molded at lower temperatures. Removal of the low molecular weight fraction enhances resin thermal stability. Moreover, it has been observed that the poly(vinyl chloride) formed by the instant invention has higher impact strength in molding compounds as compared to molding compounds containing conventional resins in the same I.V. range.

The process described above results in a poly(vinyl halide) resin with a lower polydispersity than the polymers formed via conventional free radical polymerization under similar reaction conditions. The polydispersity of the poly(vinyl halide) resin is the ratio of the weight average molecular weight to the number average molecular weight. This ratio can be summarized as $$\text{Polydispersity} = \frac{<Mw>}{<Mn>}$$

Generally, using free radical polymerization, the polydispersity of commercial poly(vinyl chloride) polymers ranges from approximately 2.2 to 3.5. In contradistinction, polydispersities of poly(vinyl chloride) formed using the process of the invention, range from approximately 1.7 to less than 2.2. A lower polydispersity enhances the mechanical properties of the resulting poly(vinyl chloride) resin by eliminating the low molecular weight fraction that has chains shorter than the critical chain entanglement length.

Polymerization of Vinyl Chloride

Example 3

Vinyl chloride (546 grams, 8.7 moles) was added to a 1 liter reactor vessel under an atmosphere of nitrogen. To this were added chloroiodomethane (0.7 g, 3.6 moles) in toluene (40 ml), and an azo initiator (0.15 mole % on vinyl chloride). The stirred reaction mixture was heated to 50° C. and allowed to react for 3 hours. The excess vinyl chloride was evaporated, and the resultant poly(vinyl chloride) filtered, washed with water and methanol and finally dried. Size-exclusion chromatography demonstrated that the product polymer had $M_n=37,000$ and $M_w/M_n=1.7$.

Example 4

A 3 liter reactor, equipped with agitation, cooling means and a bottom sampling valve, was employed for this Example. The following polymerization recipe was used with the materials charged in the order shown:

| | |
|---|---|
| Demineralized water | 158.0000 parts |
| 1-Chloro-1-iodoethane | 0.3000 parts |
| Primary dispersant PVA | 0.0750 parts |
| Hydroxymethyl cellulose | 0.0085 parts |
| Vinyl chloride monomer | 100.0000 parts |
| Peroxy ester initiator | 0.0570 parts |
| Phenolic shortstop | 0.0080 parts |

The water, primary dispersant PVA, hydroxymethyl cellulose and 1-chloro-l-iodoethane were placed in the open vessel, after which the reactor Was sealed and pressure tested. With the agitator at low speed, the reagents were vacuum purged. Then the vinyl chloride monomer was charged, the agitation increased, and the heat-up cycle commenced. When the reaction mixture had reached the polymerization temperature of 53° C., the initiator was added. This was zero time. Using the cooling jacket, the polymerization temperature was maintained at 53° C. throughout the reaction.

At selected times, samples (ca. 5–10 ml) were extracted through the sampling valve without otherwise disturbing the reaction. These were stored in a vented hood until all the excess vinyl chloride monomer had evaporated. The PVC resin was filtered, washed with water and dried at 80° C. At the end of the reaction, the bulk mixture was shortstopped, and the bulk PVC resin isolated, washed and dried. In this way, it was possible to monitor the progress of the reaction in terms of molecular weight ($M_w$, $M_n$) and polydispersity ($M_w/M_n$) of the PVC as a function of time.

The results obtained for the samples are as follows in Table 1 are illustrated graphically in FIG. 1:

TABLE 1

| Time of Sample (Mins) | Conversion % | $M_w$ | $M_n$ | $M_w/M_n$ |
|---|---|---|---|---|
| 113 | 11.0 | 49,680 | 21,860 | 2.28 |
| 190 | 22.0 | 40,860 | 21,960 | 1.86 |
| 256 | 32.0 | 46,140 | 25,820 | 1.79 |
| 317 | 42.0 | 51,700 | 28,820 | 1.80 |
| 357 | 49.0 | 56,340 | 31,580 | 1.79 |

The results clearly show the trend to higher $M_n$ and $M_w$, and to lower polydispersity or $M_w/M_n$, with increasing time/conversion. In a normal radical polymerization process for the manufacture of PVC, M.W. and polydispersity are established early in the reaction, at about 7% conversion. Thus it has been shown that by limiting monomer conversion accurate molecular weight control can be obtained. A preferred conversion level is in a range of from 20% to 80% by weight of monomer(s) converted to polymer. A novel polyvinyl halide monomer having a number average molecular weight ranging from 9,000 to 30,000 can be obtained with a conversion of less than 50% by weight using an effective amount of iodine containing chain transfer agent having the formula according to (I–V).

Example 5 (Comparative)

A 3 liter reactor, equipped with agitator, cooling means, and a dip tube for sampling purposes, was used in this Example. The following polymerization recipe was used with the ingredients charged in the order shown:

| | |
|---|---|
| Iodoform | 0.2000 parts |
| Methanol | 0.3000 parts |
| Vinyl chloride monomer | 100.0000 parts |
| Demineralized water | 160.0000 parts |
| Primary dispersant PVA | 0.0750 parts |
| Hydroxymethyl cellulose | 0.0085 parts |
| Peroxy ester initiator | 0.0570 parts |
| Phenolic shortstop | 0.0140 parts |

The iodoform and methanol were placed in the open vessel, after which the reactor was sealed. After evacuation and a nitrogen flush, the vinyl chloride monomer was added. Then the water, primary dispersant PVA, hydroxymethyl cellulose and initiator were charged. The reaction mixture was heated and maintained at 53° C.

At 50, 100 and 140 minutes after the reaction mixture had reached 53° C., samples of approximately 50 ml were extracted through the dip tube. The phenolic shortstop was then added to the reactor and, after 15 minutes, the reactor was vented. The resin samples were filtered, washed with water and dried at 80° C. The samples were analyzed by gel permeation chromatography. In this way it was possible to monitor the progress of the reaction in terms of molecular weight ($M_w$, $M_n$) and polydispersity ($M_w/M_n$) of the PVC as a function of time.

The results obtained for the Example 5 are in Table 2:

TABLE 2

Figure 2:
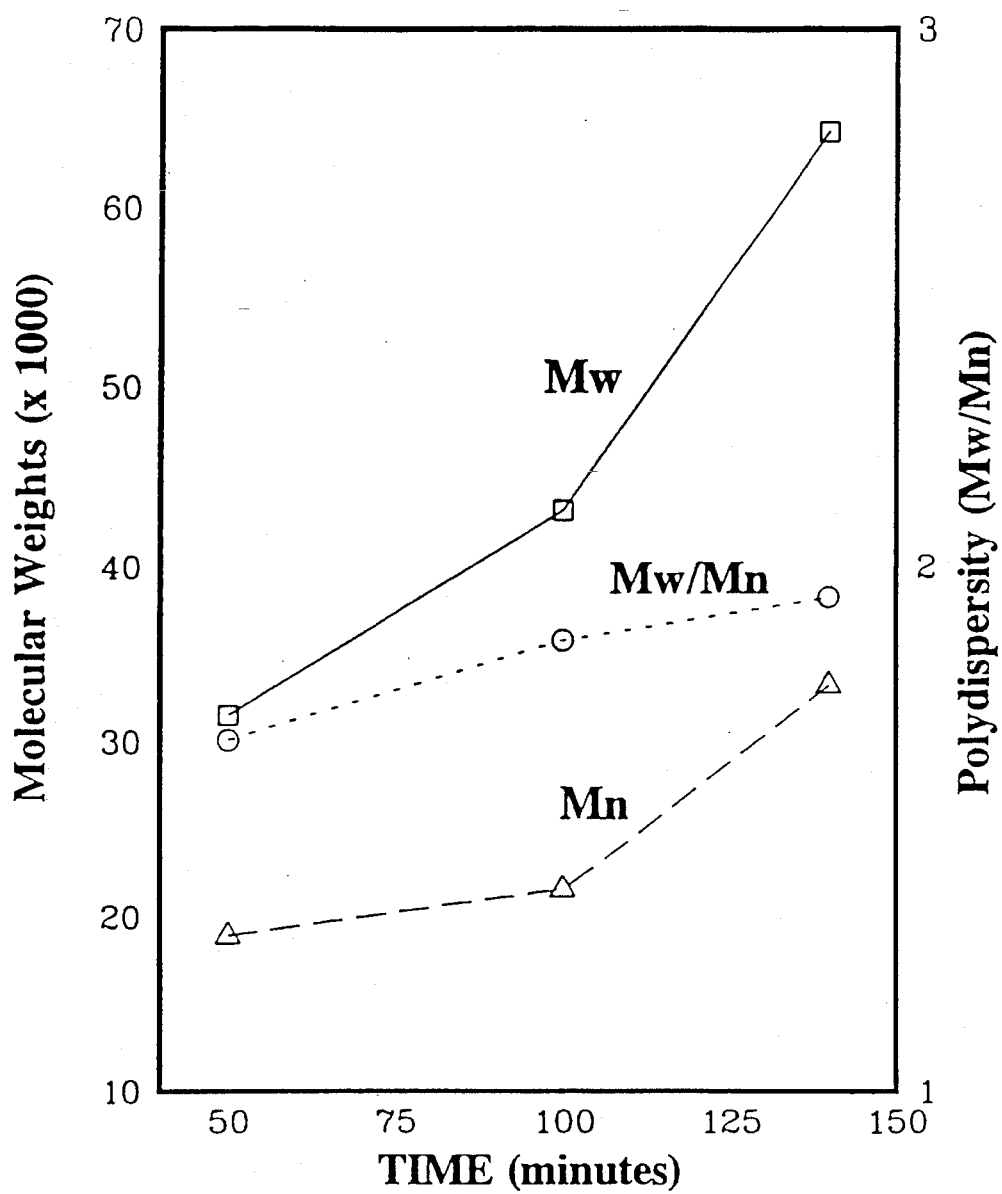
FIG. 2 is a graph showing the relationship between the weight average (Mw) and number average (Mn) molecular weight, polydispersity and conversion during the "pseudo-living" radical polymerization of vinyl chloride in the presence of 1-chloro-1-iodoethane chain transfer agent.

| Time of Sample (Mins) | Conversion % | $M_w$ | $M_n$ | $M_w/M_n$ |
|---|---|---|---|---|
| 50 | 4 | 31,500 | 18,900 | 1.67 |
| 100 | 8 | 43,200 | 21,550 | 2.00 |
| 140 | 12 | 64,200 | 33,200 | 1.94 | and are illustrated in FIG. 2. The results clearly show the trend to higher $M_n$ and $M_w$, while maintaining low polydispersity or $M_w/M_n$, with increasing time/conversion. In a normal radical polymerization process for the manufacture of PVC, M.W. and polydispersity are established early in the reaction, at about 7% conversion.

Example C6 (Control)

A 3 liter reactor, equipped with agitation and cooling means, was employed for this Example. The following polymerization recipe was used with the materials charged in the order shown:

| | |
|---|---|
| Methanol | 0.3000 parts |
| Vinyl chloride monomer | 100.0000 parts |
| Demineralized water | 160.0000 parts |
| Primery dispersant PVA | 0.0750 parts |

-continued

| | |
|---|---|
| Hydroxymethyl cellulose | 0.0085 parts |
| Peroxy ester initiator | 0.0570 parts |
| Phenolic shortstop | 0.0140 parts |

The methanol was placed in the open vessel, after which the reactor was sealed. After evacuation and a nitrogen flush, the vinyl chloride monomer was added. Then the water, primary dispersant PVA, hydroxymethyl cellulose and initiator were charged. The reaction mixture was heated and maintained at 53° C. The reaction was allowed to proceed for 400 minutes or until a pressure drop of 35 kpa was observed. A phenolic shortstop was added and after 15 minutes, the reactor was vented. The resin was then stripped and dried, following standard techniques well know in the art.

Examples 7 through 11

The procedure of Example 6 was followed, except that the iodine containing compounds listed in the Table 3 were added to the reactor before the methanol, which was used as a rinse for the weighing container of the said iodine containing compounds. The results of the polymerizations employing the iodine containing compounds are listed in Table 3.

Comparative Examples C12 through C14

The procedure of Example 6 was followed, except that the secondary alkyl iodide compounds listed in the Table 3 were added to the reactor before the methanol, which was used as a rinse for the weighing container of the said iodine containing compounds. These chain transfer agents were cited in the German Patent Disclosure by Klinkenberg et. al.

Table 3 lists the iodine containing compounds, discussed in Examples 6 through 11, and Comparative Examples 12 through 14, the parts of each used, the mole percentage for each based on vinyl chloride monomer amount charged, the inherent viscosity of the resulting PVC resins, and the polydispersity of the same resins. By comparison, it can be readily seen that the compounds used by Klinkenberg et. al. (comparative examples C12–C14) are nearly ineffective in reducing the molecular weight or narrowing the polydispersities of the resulting resins at temperatures typically employed in commercial processes, well above 0° C. Iodoform evidences more efficiency in reducing molecular weight on a molar basis, however as illustrated in examples 21–70 below there are other problems associated with it's use.

TABLE 3

| EX # | COMPOUND | PARTS (phm) | MOLE % | I.V. | $M_w/M_n$ |
|---|---|---|---|---|---|
| C6 | Control | 0 | — | 1.01 | 2.2 |
| 7 | 1-chloro-1-iodoethane | 0.32 | 0.10 | 0.58 | 1.7 |
| 8 | Iodoform | 0.32 | 0.05 | 0.36 | 1.8 |
| 9 | 1,2-diiodo-ethane | 0.32 | 0.07 | 0.46 | 2.0 |
| 10 | Benzyl Iodide | 0.32 | 0.11 | 0.36 | 1.9 |
| 11 | Iodoacet- | 0.32 | 0.12 | 0.35 | 1.8 |

TABLE 3-continued

| EX # | COMPOUND | PARTS (phm) | MOLE % | I.V. | $M_w/M_n$ |
|---|---|---|---|---|---|
| | onitrile | | | | |
| C12 | 2-Iodobutane | 0.32 | 0.11 | 0.96 | 2.3 |
| C13 | 2-Iodopropane | 0.32 | 0.12 | 1.02 | 2.2 |
| C14 | Cyclohexyl Iododide | 0.32 | 0.09 | 0.84 | 2.2 |

Example C15 (Control)

A 3 liter reactor, equipped with agitator and cooling means, was employed for this Example. The following polymerization recipe was used with the materials charged in the recited order:

| | |
|---|---|
| Methanol | 0.3000 parts |
| Vinyl chloride monomer | 100.0000 parts |
| Demineralized water | 160.0000 parts |
| Primary dispersant PVA | 0.0750 parts |
| Hydroxymethyl cellulose | 0.0090 parts |
| Peroxy ester initiators | 0.0520 parts |
| Phenolic shortstop | 0.0140 parts |

The methanol was placed in the open vessel, after which the reactor was sealed. After evacuation and a nitrogen flush, the vinyl chloride was added. Then the water, primary dispersant PVA, hydroxymethyl cellulose and initiators were charged. The reaction mixture was heated and maintained at 47° C. The reaction was allowed to proceed for 650 minutes or until a pressure drop of 35 kpa was observed. A phenolic shortstop was added and, after 15 minutes, the reactor was vented. The resin was then stripped and dried, following standard techniques well known in the art.

Example 16

The procedure of Example 15 was followed except that 0.32 parts of 1-chloro-1-iodoethane were added to the reactor before the methanol, which was used as a rinse for the weighing container of the said iodine containing compound.

Example 17

A 3 liter reactor, equipped with agitation and cooling means, was employed for this Example. The following polymerization recipe was used with the materials charged in the order shown:

| | |
|---|---|
| Demineralized water | 160.0000 parts |
| 1-Chloro-1-iodoethane | 0.3000 parts |
| Primary dispersant PVA | 0.0750 parts |
| Hydroxymethyl cellulose | 0.0085 parts |
| Vinyl chloride monomer | 100.0000 parts |
| Peroxy ester initiator | 0.0570 parts |
| phenolic shortstop | 0.0140 parts |

The water, 1-chloro-1-iodoethane, primary dispersant PVA and hydroxymethyl cellulose were placed in the open vessel, after which the reactor was sealed. After evacuation and a nitrogen flush, the vinyl chloride was added. Then the initiator was charged. The reaction mixture was heated and maintained at 53° C. The reaction was allowed to proceed for 357 minutes. A phenolic shortstop was added and, after 15 minutes, the reactor was vented. The resin was stripped and dried, following standard techniques well known in the art.

Example 18

A 3 liter reactor, equipped with agitation and cooling means, was employed for this Example. The following polymerization recipe was used, with the materials charged in the order shown:

| | |
|---|---|
| Demineralized water | 160.0000 parts |
| Primary dispersant PVA | 0.0750 parts |
| Hydroxymethyl cellulose | 0.0090 parts |
| Vinyl chloride monomer | 100.0000 parts |
| 1-chloro-1-iodoethane | 0.3160 parts |
| Peroxy ester initiator | 0.0570 parts |
| Phenolic shortstop | 0.0140 parts |

The water was placed in the open vessel, after which the reactor was sealed. After evacuation and a nitrogen flush, the primary dispersant PVA and hydroxymethyl cellulose were added. The 1-chloro-1-iodoethane was dissolved in the vinyl chloride monomer in a separate vessel, and the contents transferred to the reactor. The initiator was then charged. The reaction mixture was heated and maintained at 53° C. The reaction was allowed to proceed for 400 minutes. A phenolic shortstop was added and, after 15 minutes, the reactor was vented. The resin was then stripped and dried, following standard procedures well known in the art.

Data for the reactions in which 1-chloro-1-iodoethane was employed as a chain transfer agent, and the properties of the resulting resins, are tabulated below in Table 4

TABLE 4

| EX # | METHOD OF ADDITION | PARTS (phm) | ADDITION TIME | POLY TEMP °C. | RXN TIME (MIN) | INIT | I.V. | $M_w/M_n$ |
|---|---|---|---|---|---|---|---|---|
| 6 | A | 0 | Control | 53 | 380 | X | 1.01 | 2.24 |
| 7 | A | 0.32 | M | 53 | 400 | X | 0.58 | 1.70 |
| C15 | A | 0 | Control | 47 | 483 | Y | 1.20 | 2.25 |

TABLE 4-continued

| EX # | METHOD OF ADDITION | PARTS (phm) | ADDITION TIME | POLY TEMP °C. | RXN TIME (MIN) | INIT | I.V. | $M_w/M_n$ |
|---|---|---|---|---|---|---|---|---|
| 16 | A | 0.32 | M | 47 | 560 | Y | 0.94 | 2.14 |
| 17 | B | 0.30 | M | 53 | 357 | X | 0.47 | 1.79 |
| 18 | C | 0.32 | M | 53 | 400 | X | 0.56 | 1.98 |
| C19 | B | 0 | Control | 53 | 229 | X | 1.03 | 2.21 |

METHOD OF ADDITION OF 1-CHLORO-1-IODOETHANE:

A: Addition of 1-chloro-1-iodoethane first
B: Addition of water first
C: Predissolution of 1-chloro-1-iodoethane in VCM

ADDITION TIME FOR 1-CHLORO-1-IODOETHANE:

M: First ingredient in the reactor
N: Added together with the VCM

INITIATOR:

X: Peroxy initiator
Y: Mixture of two peroxy initiators

Example C19 (Control)

A 3 liter reactor, equipped with agitation and cooling means, was employed for this Example. The following polymerization recipe was used with the materials charged in the order shown:

| | |
|---|---|
| Demineralized water | 160.0000 parts |
| Primary dispersant PVA | 0.0750 parts |
| Hydroxymethyl cellulose | 0.0085 parts |
| Azo initiator | 0.6676 parts |
| Vinyl chloride monomer | 100.0000 parts |
| Phenolic shortstop | 0.0140 |

The water, primary dispersant PVA, hydroxymethyl cellulose and initiator were placed in the open reactor, after which the reactor was sealed. After evacuation and a nitrogen flush, the vinyl chloride monomer was added. The reaction mixture was heated and maintained at 53° C. The reaction was allowed to proceed for 500 minutes or until a pressure drop of 35 kpa was observed. A phenolic shortstop was added and, after 15 minutes, the reactor was vented. The resin was then stripped and dried, following standard techniques well known in the art. The results of Example C19 are set forth in Table 4 above.

Examples 20–51

The various sized reactors were used to prepare polyvinyl chloride using iodoform chain transfer agent. The largest reactor is employed to accurately simulate commercial scale polymerizations. The reactors, were equipped with agitation and cooling means. The following polymerization recipe was used:

| | |
|---|---|
| Demineralized water | 160.0000 parts |
| Primary dispersant PVA | 0.0750 parts |
| Hydroxymethyl cellulose | 0.0085 parts |
| Vinyl chloride monomer | 100.0000 parts |
| Peroxy ester initiator | 0.0570 parts |
| Iodoform | variable |
| Phenolic shortstop | 0.0140 parts |

The water, primary dispersant PVA and hydroxymethyl cellulose were placed in the open vessel, after which the reactor was sealed. After evacuation and a nitrogen flush, the vinyl chloride was added except where noted in Table 5 iodoform was first added in "beginning". The initiator was then charged. The mixture was heated and maintained at the poly temperature indicated. The reaction was allowed to proceed for the total time indicated in Table 5 after the reaction temperature was reached. A phenolic shortstop was then added and, after 15 minutes, the reactor was vented. The resin was then stripped and dried, following standard techniques well known in the art. The results of these Examples are listed in Table 5.

TABLE 5

| EX # | ADDN TYPE | PARTS (phm) | ADDITION TIME | POLY TEMP °C. | RXN TIME (MIN) | INIT | I.V. | $M_w/M_n$ |
|---|---|---|---|---|---|---|---|---|
| 20 | A | 0.316 | BEGINNING | 53 | 401 | EHP | .364 | 1.75 |
| 21 | A | 0 | BEGINNING | 53 | 380 | EHP | 1.01 | 2.54 |
| 22 | A | 0.1 | BEGINNING | 53 | 400 | EHP | .786 | 2.36 |
| 23 | A | 0 | BEGINNING | 53 | 400 | EHP | .999 | 2.15 |
| 24 | A | 0.05 | BEGINNING | 53 | 401 | EHP | .931 | 2.40 |
| 25 | A | 0.2 | BEGINNING | 53 | 400 | EHP | .661 | 2.10 |
| 26 | A | 0.25 | BEGINNING | 53 | 400 | EHP | .665 | — |
| 27 | A | 0.25 | BEGINNING | 53 | 400 | EHP | .518 | 1.96 |
| 28 | A | 0.2 | BEGINNING | 53 | — | EHP | — | — |
| 29* | A | 0.25 | BEGINNING | 53 | 1000 | EHP | — | — |
| 30* | A | 0.25 | BEGINNING | 53 | 1000 | — | — | — |
| 31 | D | 0.25 | AT RXN TEMP | 53 | 400 | EHP | .647 | 2.07 |
| 32 | A | 0.25 | BEGINNING | 53 | 400 | EHP | .377 | 1.86 |
| 33 | B | 0.25 | AT 52° C. | 53 | 400 | EHP | .634 | 2.09 |

TABLE 5-continued

| EX # | ADDN TYPE | PARTS (phm) | ADDITION TIME | POLY TEMP °C. | RXN TIME (MIN) | INIT | I.V. | $M_w/M_n$ |
|---|---|---|---|---|---|---|---|---|
| 34* | C | 0.25 | AT 52° C. | 53 | 500 | EHP | — | — |
| 35 | D | 0.25 | AT RXN TEMP | 53 | 500 | EHP | .567 | 1.86 |
| 36 | E | 0.25 | AT RXN TEMP | 53 | 500 | EHP | .670 | 2.09 |
| 37 | C | 0.25 | AT 400 MIN. | 53 | 500 | EHP | .992 | 2.29 |
| 38* | B | 0.25 | WITH VCM | 53 | 400 | EHP | — | — |
| 39* | B | 0.25 | WITH VCM | 53 | 400 | EHP | — | — |
| 40* | B | 0.25 | WITH VCM | 53 | 400 | EHP | — | — |
| 41 | C | 0.25 | AT 52° C. | 53 | 500 | EHP | .414 | 1.77 |
| 42* | A | 0.25 | BEGINNING | 53 | 415 | ACPP | — | — |
| 43* | A | 0.25 | BEGINNING | 53 | 400 | ACPP | — | — |
| 44 | C | 0.25 | AT 300 MIN. | 53 | 500 | EHP | .982 | 2.14 |
| 45* | B | 0.25 | WITH VCM | 53 | 500 | AIBN | — | — |
| 46 | B | 0.25 | WITH VCM | 53 | 354 | AIBN | .698 | 2.20 |
| 47 | E | 0.25 | AT RXN TEMP | 53 | 500 | EHP | .579 | 2.03 |
| 48 | F | 0.25 | AT RXN TEMP | 53 | 598 | EHP | .788 | 2.25 |
| 49^ | B | 0.25 | WITH VCM | 53 | 279 | AIBN | — | — |
| 50 | B | 0.25 | WITH VCM | 53 | 290 | AIBN | .706 | 2.11 |
| 51 | B | 0.25 | WITH VCM | 53 | 500 | AIBN | .426 | 1.86 |
| 52 | B | 0.25 | WITH VCM | 53 | 500 | AIBN | .461 | 1.83 |
| 53 | B | 0.25 | WITH VCM | 53 | 276 | AIBN | .735 | 2.13 |
| 54 | B | 0.25 | WITH VCM | 53 | 288 | AIBN | .735 | 2.18 |
| 55 | B | 0 | CONTROL | 53 | 229 | AIBN | 1.02 | 2.21 |
| 56 | F | 0.25 | AT RXN TEMP | 53 | 600 | EHP | .787 | 2.12 |
| 57 | E | 0.25 | AT RXN TEMP | 53 | 500 | EHP | .702 | 2.08 |
| 58^ | G | 0.25 | WITH VCM | 53 | 400 | EHP | — | — |
| 59 | B | 0.25 | WITH VCM | 40 | 800 | ACND | .285 | 2.38 |
| 60 | G | 0.25 | WITH VCM | 40 | 800 | EHP | .346 | 1.84 |
| 61* | H | 0.25 | WITH VCM | 53 | 400 | EHP | — | — |
| 62^ | H | 0.25 | WITH VCM | 53 | 401 | EHP | .645 | — |
| 63^ | G | .10 | WITH VCM | 40 | 800 | ACND | .453 | — |
| 64 | B | 0 | CONTROL | 40 | 455 | ACND | 1.39 | — |
| 65* | B | 0.10 | WITH VCM | 40 | 400 | ACND | — | — |
| 66^ | H | 0.25 | WITH VCM | 53 | 800 | EHP | .648 | — |
| 67^ | B | 0.05 | WITH VCM | 40 | 800 | ACND | 1.22 | 2.20 |
| 68 | B | .316 | WITH VCM | 53 | 400 | EHP | — | — |
| 69 | B | .316 | WITH VCM | 53 | 400 | EHP | — | — |
| 70 | A | .30 | BEGINNING | 53 | 400 | EHP | — | — |

*-NO YIELD OBTAINED
^-COLLOIDAL UPSET-SOLID CHARGE

METHOD OF ADDITION OF IODOFORM:

A: Addition of iodoform first
B: Predissolution of iodoform in VCM
C: Rapid metering
D: Metering over 300 minutes
E: Metering over 375 minutes
F: Metering over 450 minutes G: R
educed oxygen vented vinyl monomer
H: Reduced oxygen/entire dispersion de-aerated

INITIATOR:

EHP= peroxydicarbonate initiator
AIBN= azo initiator
ACND= peroxyester initiator Table 5 illustrates unacceptable erratic results obtained using iodoform at typical temperatures used in commercial processes. A variety of charging procedures and operating conditions were attempted and no suitable conditions were found to alleviate the inconsistent effectiveness of iodoform. Examples 29, 30, 34, 38–40, 42, 43, 45, 61, and 65 evidence no conversion of monomer. Examples 49, 58, 62, 63, 66, and 67 result in a solid charge with no useable product. Examples 37, 44, 53, and 56 resulted in poor molecular weight reduction and very little or no reduction in polydispersity.

In contrast to the results obtained using iodoform, 46 successive polymerizations of vinyl chloride were undertaken using 1-chloro-1-iodoethane with no adverse affects and consistent results ware obtained. The amount of 1-chloro-1-ethane used ranged from 0.1 to 0.6 weight parts per 100 weight parts monomer successfully and in high yield. As previously noted, the extent of molecular weight reduction can be controlled by the extent of monomer conversion. Commercially acceptable yields can be obtained with consistent results and acceptable control of molecular weight and polydispersity is obtainable using the chain transfer agents having the structures defined by (I)–(V) above.

DEHYDROCHLORINATION TESTING OF RESINS

Solid state thermal stability data on random PVC resins from the above Examples is set out below in Table 6. This was obtained via dehydrochlorination studies of the unstabilized resins at 190° C. under nitrogen atmosphere. The higher the measured rate of dehydrochlorination (i.e. loss of available Hcl), the less thermally stable the resin.

By way of the most appropriate comparison, the solid state thermal stability is presented for industrial PVC resins, having $M_n=28,000$ and I.V.=0.52, and $M_n=65,000$ and I.V. 1.02, manufactured without the intervention of any chain transfer processes.

TABLE 6

| PVC RESIN | I.V | DEHYDRO-CHLORINATION RATE *%Hcl/MIN) × $10^{-3}$ |
| --- | --- | --- |
| Commercial PVC | 1.02 | 17.0 |
| Commercial PVC | 0.52 | 27.7 |
| Example C6 | 1.01 | 14.2 |
| Example 8 | 0.46 | 21.9 |
| Example 10 | 0.36 | 12.2 |
| Example C12 | 0.196 | 12.8 |
| Example C13 | 1.02 | 11.1 |
| Example C15 | 1.20 | 9.7 |
| Example 16 | 0.94 | 9.7 |
| Example 18 | 0.56 | 14.6 |
| Example C19 | 0.522 | 15.6 |
| Example 35 | 0.56 | 27.6 |

The above data shows predominately low solid state dehydrochlorination rates and time, hence better thermal stability.

From the foregoing description, one skilled in the art can easily ascertain the essential characteristic of this invention and without departing from the spirit and scope thereof can make various changes and modification of the invention to adapt it to various usages and conditions.

We claim:

1. An improved industrial aqueous process for preparing poly(vinyl halide) polymers having a molecular weight of from 9,000 to 32,000 above 0° C. by free radical polymerization, comprising the steps of:

(a) adding a portion or all vinyl halide monomer to be polymerized and optional ethylenic unsaturated comonomer(s), to a polymerizer, along with one or more dispersants, (b) adding a free-radical generating initiator, (c) polymerizing said monomer and optional comonomer(s) in the presence of from 0.1 to 1.0 weight parts per 100 weight parts of said monomer and comonomer(s) of a chain transfer agent selected from the group consisting of chloroiodomethane, 1-chloro-1-iodoethane, 1-chloro-1,2 diiodoethane, 1,3-dichloro-1-iodopropane, 1-chloro-1-iodo-3-phenyl propane, methylcyclohexyl iodide, iodoacetonitrile, and 1,2-diiodoethane, (d) and converting from 20% to 99.9% by weight of said monomer and optional comonomer(s) to polymer, said polymer comprising at least 50 weight % of repeating units of vinyl chloride.

* * * * *